United States Patent
Lei et al.

(10) Patent No.: US 9,532,933 B2
(45) Date of Patent: Jan. 3, 2017

(54) MICROCAPSULES CONTAINING ACTIVE INGREDIENTS

(71) Applicant: International Flavors & Fragrances Inc., New York, NY (US)

(72) Inventors: Yabin Lei, Holmdel, NJ (US); Lewis Michael Popplewell, Morganville, NJ (US); Xiao Huang, Freehold, NJ (US)

( * ) Notice: Subject to any disclaimer, the term of this patent is extended or adjusted under 35 U.S.C. 154(b) by 0 days.

(21) Appl. No.: 14/631,969

(22) Filed: Feb. 26, 2015

(65) Prior Publication Data

US 2015/0164751 A1 Jun. 18, 2015

Related U.S. Application Data

(63) Continuation of application No. 12/793,911, filed on Jun. 4, 2010, now Pat. No. 9,044,732, which is a continuation-in-part of application No. 12/328,340, filed on Dec. 4, 2008, now abandoned.

(51) Int. Cl.

| | | |
|---|---|---|
| A61K 8/11 | (2006.01) |
| A61K 8/02 | (2006.01) |
| B01J 13/18 | (2006.01) |
| C11D 3/50 | (2006.01) |
| A61K 8/27 | (2006.01) |
| A61K 8/41 | (2006.01) |
| A61K 8/46 | (2006.01) |
| A61K 8/58 | (2006.01) |
| A61K 8/84 | (2006.01) |
| A61K 8/92 | (2006.01) |
| A61Q 5/02 | (2006.01) |
| A61Q 15/00 | (2006.01) |
| A61Q 19/10 | (2006.01) |
| A61K 8/40 | (2006.01) |
| A61Q 13/00 | (2006.01) |

(52) U.S. Cl.
CPC ............... *A61K 8/0245* (2013.01); *A61K 8/11* (2013.01); *A61K 8/27* (2013.01); *A61K 8/40* (2013.01); *A61K 8/416* (2013.01); *A61K 8/463* (2013.01); *A61K 8/585* (2013.01); *A61K 8/84* (2013.01); *A61K 8/92* (2013.01); *A61Q 5/02* (2013.01); *A61Q 13/00* (2013.01); *A61Q 15/00* (2013.01); *A61Q 19/10* (2013.01); *B01J 13/18* (2013.01); *C11D 3/505* (2013.01); *A61K 2800/10* (2013.01); *A61K 2800/56* (2013.01); *A61K 2800/622* (2013.01)

(58) Field of Classification Search
CPC .............................. A61K 2300/00; A61K 9/50
USPC ......................................... 424/490, 489, 492
See application file for complete search history.

(56) References Cited

U.S. PATENT DOCUMENTS

| | | | | |
|---|---|---|---|---|
| 2002/0064541 | A1* | 5/2002 | Lapidot | A61K 8/042 424/401 |
| 2007/0202063 | A1* | 8/2007 | Dihora | A61K 8/11 424/70.1 |

OTHER PUBLICATIONS von Phul S.; product information from D-form Inc., Title: Antifoam, product information from D-form Inc., published online Mar. 1, 2004.*
Iijima et al. (Non-paten literature: KONA Powder and Particle Journal, No. 27, pp. 119-129, 2009.*
SK Ghosh; title: Functional Coatings and Microencapsulation: A General Perspective, published Jun. 29, 2006, obtained from onlinelibrary.wiley.com.*

* cited by examiner

*Primary Examiner* — Yanzhi Zhang
(74) *Attorney, Agent, or Firm* — Martin Zhang; XuFan Tseng; Elizabeth M. Stover

(57) ABSTRACT

The present invention relates to a microcapsule particle composition that is composed of a sol-gel material. The microcapsule particle composition is well suited for personal care and cleaning products.

30 Claims, 5 Drawing Sheets

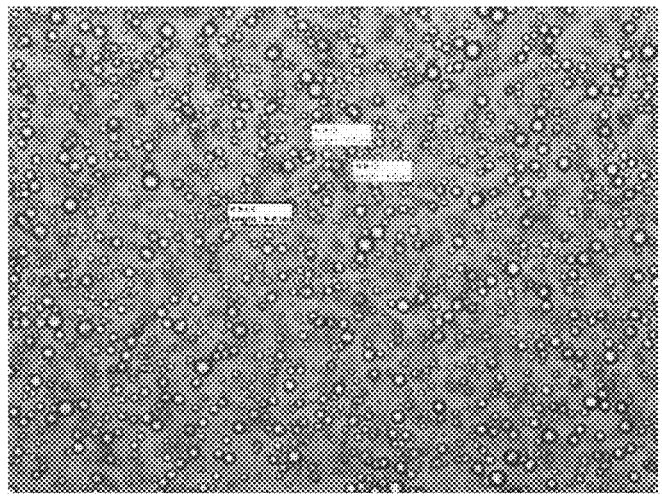
*Figure 1. Optical microscopy image of standard silica capsules dispersed in DI $H_2O$ as fresh sample.*
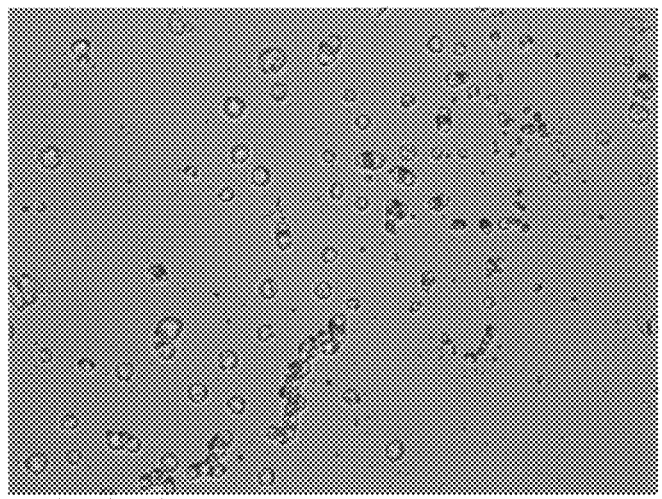
*Figure 2. Optical microscopy image of standard silica capsules dried overnight on glass slide shows complete breakage.*

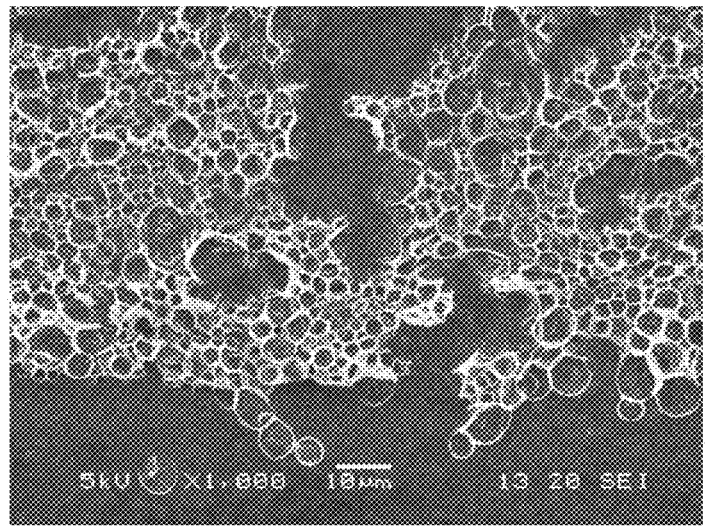
*Figure 3. SEM image of dried standard silica capsules shows breakage.*
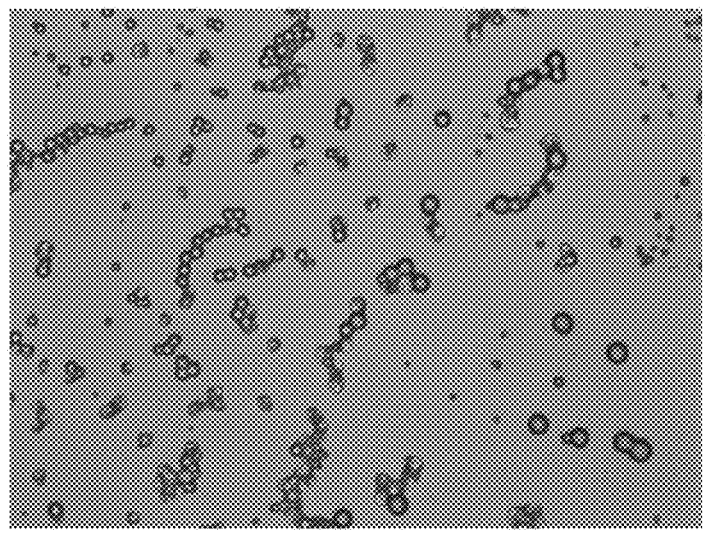
*Figure 4. Optical microscopy image of polyethleneimine PEI-treated silica capsules dried overnight on glass slide.*

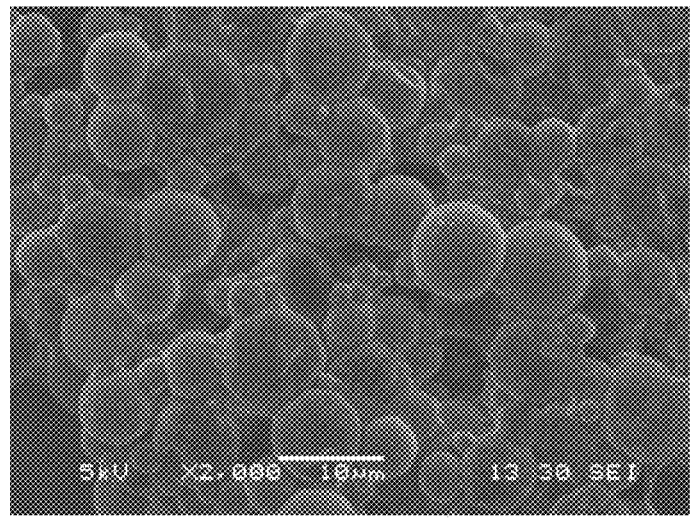
*Figure 5. SEM image of dried polyethleneimine PEI-treated silica capsules*
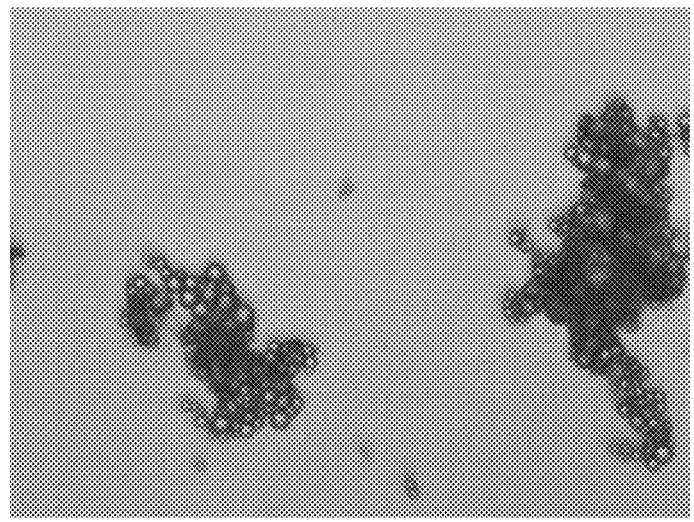
*Figure 6: Optical microscopy image of cocoamidopropylamine oxide special-treated silica capsules, 4 days after drying on glass slide.*

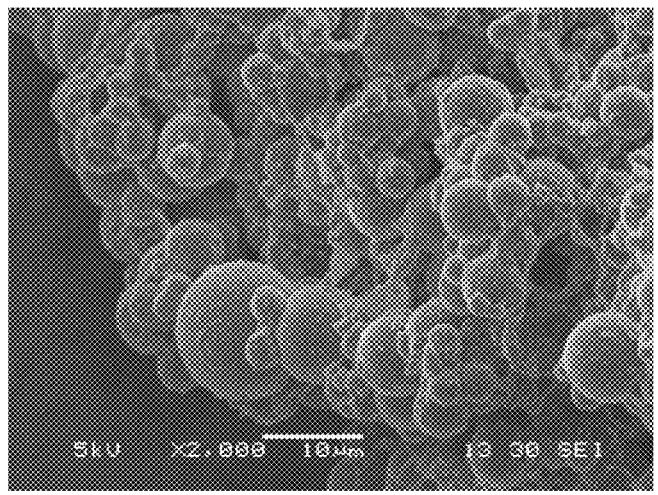
Figure 7 SEM of dried cocoamidopropylamine oxide Special-treated silica capsules
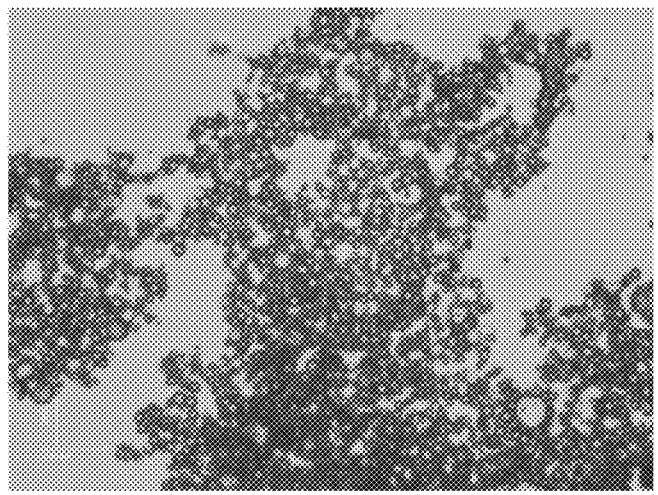
Figure 8. Optical microscopy image of zinc oxide, Z-COTE HP1 Special-treated silica capsules, 3 days after drying on glass slide.

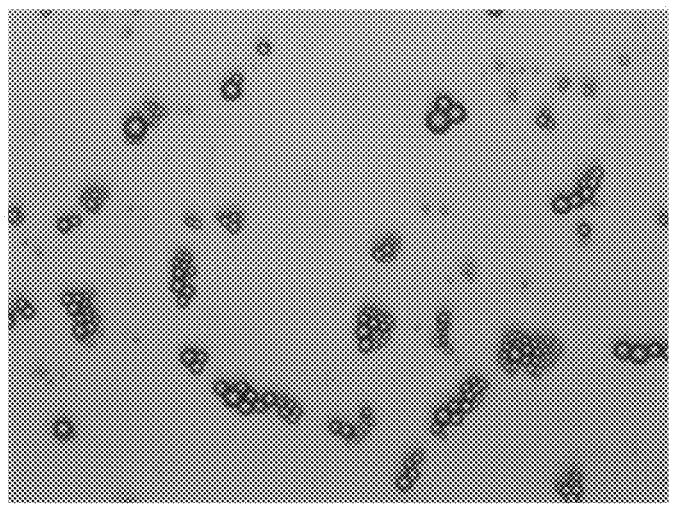
Figure 9. Optical microscopy image of STEOL CA-330-treated silica capsules, 4 days after drying on glass slide.

MICROCAPSULES CONTAINING ACTIVE INGREDIENTS

This application is a continuation of U.S. Ser. No. 12/793,911 filed on Jun. 4, 2010, which is a continuation-in-part of U.S. Ser. No. 12/328,340 filed on Dec. 4, 2008. The contents of both applications are hereby incorporated by reference in their entirety.

FIELD OF THE INVENTION

The present invention relates to active materials that are encapsulated with a sol-gel material. The microcapsule particle composition is well suited for applications associated with personal care and cleaning products.

BACKGROUND OF THE INVENTION

Fragrance chemicals are used in numerous products to enhance the consumer's enjoyment of a product. Fragrance chemicals are added to consumer products such as laundry detergents, fabric softeners, soaps, detergents, personal care products, such as but not limited to shampoos, body washes, deodorants and the like, as well as numerous other products.

In order to enhance the effectiveness of the fragrance materials for the user, various technologies have been employed to enhance the delivery of the fragrance materials at the desired time. One widely used technology is encapsulation of the fragrance material in a protective coating. Frequently the protective coating is a polymeric material. The polymeric material is used to protect the fragrance material from evaporation, reaction, oxidation or otherwise dissipating prior to use. A brief overview of polymeric encapsulated fragrance materials is disclosed in the following U.S. patents: U.S. Pat. No. 4,081,384 discloses a softener or anti-stat core coated by a polycondensate suitable for use in a fabric conditioner; U.S. Pat. No. 5,112,688 discloses selected fragrance materials having the proper volatility to be coated by coacervation with micro particles in a wall that can be activated for use in fabric conditioning; U.S. Pat. No. 5,145,842 discloses a solid core of a fatty alcohol, ester, or other solid plus a fragrance coated by an aminoplast shell; and U.S. Pat. No. 6,248,703 discloses various agents including fragrance in an aminoplast shell that is included in an extruded bar soap.

While encapsulation of fragrance in a polymeric shell can help prevent fragrance degradation and loss, it is often not sufficient to significantly improve fragrance performance in consumer products. Therefore, methods of aiding the deposition of encapsulated fragrances have been disclosed. U.S. Pat. No. 4,234,627 discloses a liquid fragrance coated with an aminoplast shell further coated by a water insoluble meltable cationic coating in order to improve the deposition of capsules from fabric conditioners. U.S. Pat. No. 6,194,375 discloses the use of hydrolyzed polyvinyl alcohol to aid deposition of fragrance-polymer particles from wash products. U.S. Pat. No. 6,329,057 discloses use of materials having free hydroxy groups or pendant cationic groups to aid in the deposition of fragranced solid particles from consumer products.

In addition, the prior art discloses the use of silica to form microcapsule formulations specifically designed to prevent an encapsulated active ingredient from leaving the microcapsule. This is desirable when the active ingredient is an irritant to the body tissue to which it is applied. It is also is desired when the active ingredient acts by interaction with light, such as sunlight. However, U.S. Pat. No. 6,303,149 fails to disclose compositions and methods for releasing and hence delivering the active ingredients. Despite these and many other disclosures there is an ongoing need for the improved delivery of fragrance materials for various personal care products, rinse-off products and leave-on products that provide improved performance.

SUMMARY OF THE INVENTION

According to one aspect of the present invention, a process is provided for preparing microcapsule particle composition having a core material encapsulated within a microcapsular shell. The core material may contain at least one active ingredient, such as but not limited to a fragrance. The process comprises the steps of first mixing an appropriate amount sol-gel precursor and fragrance oil, followed by cooling of the mixture obtained. The next step in the process is to prepare a surfactant solution by dissolving an appropriate amount of surfactant in water and then cooling the surfactant solution. In the next step the sol-gel precursor and fragrance oil are added to the surfactant solution and then the mixture is homogenized. A defoamer is added as needed and the mixture is allowed to cure to form the microcapsule particle composition.

In another embodiment, a process is provided for preparing microcapsule particle composition having a core material encapsulated within a microcapsular shell. The core material may contain at least one active ingredient such as but not limited to a fragrance. In the first step of the process a fragrance oil is added to an aqueous surfactant solution. The mixture is homogenized to form a fragrance emulsion and then sol-gel precursor is added dropwise to the fragrance emulsion under continuous mixing. The final mixture is allowed to cure, e.g., at room temperature, to form the microcapsule particle composition.

In yet another embodiment, a process for preparing microcapsule particle composition having a core material encapsulated within a microcapsular shell is provided. The microcapsules prepared according to this process may contain a core material, which may contain at least one active ingredient such as, but not limited to a fragrance. The first step of the process is to add an appropriate amount of fragrance oil to an aqueous surfactant solution and then homogenize the mixture to form a fragrance emulsion. An appropriate amount of water is added to the fragrance emulsion to achieve the desired concentration. Then an appropriate amount of sol-gel precursor is added to the to the diluted fragrance emulsion dropwise under constant mixing. The mixture is then allowed to cure, e.g., at room temperature, until the microcapsule particle composition is formed.

In still another embodiment a process is provided for preparing a microcapsule particle composition having a core material encapsulated within a microcapsular shell. The core material comprises at least one active ingredient such as but not limited to a fragrance. The first step of the process is to prepare a fragrance emulsion by emulsifying an appropriate amount of fragrance oil into surfactant solution. The second step is to prepare a sol-gel precursor emulsion by emulsifying an appropriate amount of sol-gel precursor and an aqueous surfactant solution. The next step is to add the sol-gel precursor emulsion to the fragrance emulsion under constant mixing and then allow the final mixture to cure, e.g., at room temperature, until capsule have formed.

In an additional embodiment of the invention a process is provided for preparing microcapsule particle composition having a core material encapsulated within a microcapsular shell, wherein the core material may contain at least one active ingredient such as but not limited to fragrance oil. The process comprises the steps of adding fragrance oil to an aqueous surfactant and homogenizing the mixture to provide a fragrance emulsion. An appropriate amount of water is added to the fragrance emulsion to achieve the desired concentration. The next step in the process is to prepare a sol-gel precursor emulsion by emulsifying sol-gel precursor into an aqueous surfactant solution. The sol-gel precursor emulsion is then added to the fragrance emulsion under constant mixing and then allowed to cure at room temperature until capsules have formed.

In another embodiment of the invention, a microcapsule particle composition having a core material encapsulated within a microcapsular shell is provided. According to this embodiment the wall material of the microcapsule is composed of a sol-gel precursor.

In yet a further embodiment a personal care composition containing the microcapsule composition is provided.

In still a further embodiment a personal care product is provided containing the microcapsule composition of the present invention.

In an embodiment of the invention a process is provided for preparing a silica microcapsule composition modified with a second sphere complexation.

The second sphere complexation may be selected from polyethyleneimine PEI, an amine oxide, cocoamidopropylamine oxide, ammonium lauryl ether sulfate, inorganic zinc oxide and mixtures thereof.

The modified capsule in the current invention delivers superior consumer befits when compared to the use of neat fragrance.

BRIEF DESCRIPTION OF THE DRAWINGS

FIG. 1. Optical microscopy image of standard silica capsules dispersed in DI H$_2$O as fresh sample.

FIG. 2. Optical microscopy image of standard silica capsules dried overnight on glass slide shows complete breakage.

FIG. 3. SEM image of dried standard silica capsules shows breakage.

FIG. 4. Optical microscopy image of polyethyleneimine treated silica capsules dried overnight on glass slide.

FIG. 5. SEM image of dried polyethyleneimine treated silica capsules

FIG. 6. Optical microscopy image of cocoamidopropylamine oxide Special-treated silica capsules, 4 days after drying on glass slide.

FIG. 7. SEM of dried cocoamidopropylamine oxide special-treated silica capsules

FIG. 8. Optical microscopy image of zinc oxide special-treated silica capsules, 3 days after drying on glass slide FIG. 9. Optical microscopy image of ammonium lauryl ether sulfate-treated silica capsules, 4 days after drying on glass slide.

DETAILED DESCRIPTION OF THE INVENTION

According to the present invention a process is provided for preparing microcapsule particle composition, having a core material encapsulated within a microcapsular shell. The core material comprises at least one active ingredient, such as but not limited to a fragrance. The process comprises the steps of first mixing an appropriate amount sol-gel precursor and fragrance oil, followed by cooling of the mixture obtained. The next step in the process is to prepare a surfactant solution by dissolving an appropriate amount of surfactant in water and then cooling the surfactant solution. In the next step the sol-gel precursor and fragrance oil are added to the surfactant solution and then the mixture is homogenized. A defoamer is added as needed and the mixture is allowed to cure to form the capsule particles.

In another embodiment, a process is provided for preparing microcapsule particle composition having a core material encapsulated within a microcapsular shell, wherein the core material may contain at least one active ingredient such as but not limited to a fragrance. In the first step of the process a fragrance oil is added to an aqueous surfactant solution. The mixture is homogenized to form a fragrance emulsion and then sol-gel precursor is added dropwise to the fragrance emulsion under continuous mixing. The final mixture is allowed to cure, e.g., at room temperature, to form capsule particles.

In yet another embodiment, a process for preparing microcapsule particle composition having a core material encapsulated within a microcapsular shell is provided. The microcapsules prepared according to this process may contain at least one active ingredient such as but not limited to a fragrance. The first step of the process is to add an appropriate amount of fragrance oil to an aqueous surfactant solution and then homogenize the mixture to form a fragrance emulsion. An appropriate amount of water is added to the fragrance emulsion to achieve the desired concentration. Then an appropriate amount of sol-gel precursor is added to the to the diluted fragrance emulsion dropwise under constant mixing. The mixture is then allowed to cure, e.g., at room temperature, until capsules are formed.

In still another embodiment a process is provided for preparing microcapsules having a core material encapsulated within a microcapsular shell, wherein the core material comprises at least one active ingredient such as but not limited to a fragrance.

The first step of the process is to prepare a fragrance emulsion by emulsifying an appropriate amount of fragrance oil into surfactant solution. The second step is to prepare a sol-gel precursor emulsion by emulsifying an appropriate amount of sol-gel precursor and an aqueous surfactant solution. The next step is to add the sol-gel precursor emulsion to the fragrance emulsion under constant mixing and then allow the final mixture to cure, e.g., at room temperature, until capsule have formed In an additional embodiment of the invention a process is provided for preparing microcapsule particle composition having a core material encapsulated within a microcapsule shell, wherein the core material comprises at least one active ingredient such as, but not limited to fragrance oil. The process comprises the steps of adding fragrance oil to an aqueous surfactant and homogenizing the mixture to provide a fragrance emulsion. An appropriate amount of water is added to the fragrance emulsion to achieve the desired concentration. The next step in the process is to prepare a sol-gel precursor emulsion by emulsifying sol-gel precursor into an aqueous surfactant solution. The sol-gel precursor emulsion is then added to the fragrance emulsion under constant mixing and then allowed to cure, e.g., at room temperature, until capsules have formed.

In an embodiment of the invention a process is provided for preparing a silica microcapsule particle composition with a second sphere complexation.

The second sphere complexation may be selected from polyethyleneimine PEI, an amine oxide, cocoamidopropylamine oxide, ammonium lauryl ether sulfate, inorganic zinc oxide and mixtures thereof.

According to one embodiment of the present invention, the core material may contain an active ingredient, such as, but not limited to a fragrance. The fragrances suitable for use in this invention include without limitation, any combination of fragrance, essential oil, plant extract or mixture thereof that is compatible with, and capable of being encapsulated by a monomer or a polymer.

Many types of fragrances can be employed in the present invention, the only limitation being the compatibility and ability to be encapsulated by the polymer being employed, and compatibility with the encapsulation process used. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal scents such as rosemary, thyme, and sage; and woodland scents derived from pine, spruce and other forest smells. Fragrances may also be derived from various oils, such as essential oils, or from plant materials such as peppermint, spearmint and the like. Other familiar and popular smells can also be employed such as baby powder, popcorn, pizza, cotton candy and the like in the present invention.

A list of suitable fragrances is provided in U.S. Pat. Nos. 4,534,891, 5,112,688 and 5,145,842. Another source of suitable fragrances is found in Perfumes Cosmetics and Soaps, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of fragrance in the microcapsule varies from about 5 to about 95 weight percent, preferably from about 30 to about 95 and most preferably from about 50 to about 90 weight percent on a dry basis. In addition to the fragrance other agents can be used in conjunction with the fragrance and are understood to be included.

As noted above, the fragrance may also be combined with a variety of solvents which serve to increase the compatibility of the various materials, increase the overall hydrophobicity of the blend, influence the vapor pressure of the materials, or serve to structure the blend. Solvents performing these functions are well known in the art and include mineral oils, triglyceride oils, silicone oils, fats, waxes, fatty alcohols, diisodecyl adipate, and diethyl phthalate among others.

A common feature of many encapsulation processes is that they require the fragrance material to be encapsulated to be dispersed in aqueous solutions of polymers, pre-condensates, surfactants, and the like prior to formation of the capsule walls. Therefore, materials having low solubility in water, such as highly hydrophobic materials are preferred, as they will tend to remain in the dispersed perfume phase and partition only slightly into the aqueous solution. Fragrance materials with Clog P values greater than 1, preferably greater than 3, and most preferably greater than 5 will thus result in micro-capsules that contain cores most similar to the original composition, and will have less possibility of reacting with materials that form the capsule shell. Surfactants contemplated for use in the present invention may be anionic, nonionic or cationic surfactants.

One object of the present invention is to deposit capsules containing fragrance cores on desired substrates such as cloth, hair, and skin during washing and rinsing processes. Further, it is desired that, once deposited, the capsules release the encapsulated fragrance either by diffusion through the capsule wall, via small cracks or imperfections in the capsule wall caused by drying, physical, or mechanical means, or by large-scale rupture of the capsule wall. In each of these cases, the volatility of the encapsulated perfume materials is critical to both the speed and duration of release, which in turn control consumer perception. Thus, fragrance chemicals which have higher volatility as evidenced by normal boiling points of less than 250° C., preferably less than about 225° C. are preferred in cases where quick release and impact of fragrance is desired. Conversely, fragrance chemicals that have lower volatility (boiling points greater than 225° C.) are preferred when a longer duration of aroma is desired. Of course, fragrance chemicals having varying volatility may be combined in any proportions to achieve the desired speed and duration of perception.

In order to provide the highest fragrance impact from the fragrance encapsulated capsules deposited on the various substrates referenced above, it is preferred that materials with a high odor-activity be used. Materials with high odor-activity can be detected by sensory receptors at low concentrations in air, thus providing high fragrance perception from low levels of deposited capsules. This property must be balanced with the volatility as described above. Some of the principles mentioned above are disclosed in U.S. Pat. No. 5,112,688.

The following fragrance ingredients provided in Table I are among those suitable for inclusion within the capsule of the present invention:

TABLE 1

| PERFUME INGREDIENTS | CLOGP |
|---|---|
| Allyl cyclohexane propionate | 3.935 |
| Ambrettolide | 6.261 |
| Amyl benzoate | 3.417 |
| Amyl cinnamate | 3.771 |
| Amyl cinnamic aldehyde | 4.324 |
| Amyl cinnamic aldehyde dimethyl acetal | 4.033 |
| Iso-amyl salicylate | 4.601 |
| Aurantiol (Trade name for Hydroxycitronellal-methylanthranilate) | 4.216 |
| Benzyl salicylate | 4.383 |
| para-tert-Butyl cyclohexyl acetate | 4.019 |
| Iso butyl quinoline | 4.193 |
| beta-Caryophyllene | 6.333 |
| Cadinene | 7.346 |
| Cedrol | 4.530 |
| Cedryl acetate | 5.436 |
| Cedryl formate | 5.070 |
| Cinnamyl cinnamate | 5.480 |
| Cyclohexyl salicylate | 5.265 |
| Cyclamen aldehyde | 3.680 |
| Diphenyl methane | 4.059 |
| Diphenyl oxide | 4.240 |
| Dodecalactone | 4.359 |
| Iso E Super (Trade name for 1-(1,2,3,4,5,6,7,8-Octahydro-2,3,8,8-tetramethyl-2-naphthalenyl)-ethanone) | 3.455 |

TABLE 1-continued

| PERFUME INGREDIENTS | CLOGP |
|---|---|
| Ethylene brassylate | 4.554 |
| Ethyl undecylenate | 4.888 |
| Exaltolide (Trade name for 15-Hydroxyentadecanloic acid, lactone) | 5.346 |
| Galaxolide (Trade name for 1,3,4,6,7,8-Hexahydro-4,6,6,7,8,8-hexamethylcyclopenta-gamma-2-benzopyran) | 5.482 |
| Geranyl anthranilate | 4.216 |
| Geranyl phenyl acetate | 5.233 |
| Hexadecanolide | 6.805 |
| Hexenyl salicylate | 4.716 |
| Hexyl cinnamic aldehyde | 5.473 |
| Hexyl salicylate | 5.260 |
| Alpha-Irone | 3.820 |
| Lilial (Trade name for para-tertiary-Butyl-alpha-methyl hydrocinnamic aldehyde) | 3.858 |
| Linalyl benzoate | 5.233 |
| Methyl dihydrojasmone | 4.843 |
| Gamma-n-Methyl ionone | 4.309 |
| Musk indanone | 5.458 |
| Musk tibetine | 3.831 |
| Oxahexadecanolide-10 | 4.336 |
| Oxahexadecanolide-11 | 4.336 |
| Patchouli alcohol | 4.530 |
| Phantolide (Trade name for 5-Acetyl-1,1,2,3,3,6-hexamethyl indan) | 5.977 |
| Phenyl ethyl benzoate | 4.058 |
| Phenylethylphenylacetate | 3.767 |
| Phenyl heptanol | 3.478 |
| Alpha-Santalol | 3.800 |
| Thibetolide (Trade name for 15-Hydroxypentadecanoic acid, lactone) | 6.246 |
| Delta-Undecalactone | 3.830 |
| Gamma-Undecalactone | 4.140 |
| Vetiveryl acetate | 4.882 |
| Ylangene | 6.268 |
| Methyl Beta Napthyl Ketone | 1.99 |
| Terpeneol Couer | 2.67 |
| Geraniol | 2.7 |
| Dihydromyrcenol | 2.99 |
| Citronellol 950 | 3.3 |
| Tetrahydromyrcenol | 3.54 |

The higher ClogP materials are preferred, meaning that those materials with a ClogP value of 4.5 are preferred over those fragrance materials with a ClogP of 4; and those materials are preferred over the fragrance materials with a ClogP of 3.3.

The fragrance formulation of the present invention can have at least about 40 weight percent of materials with ClogP greater than 3.3, preferably greater than about 80 and more preferably greater than about 90 weight percent of materials with ClogP greater than 4.

In an additional embodiment the fragrance formulation may contain fragrance materials with a ClogP greater than about 1.5.

Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will comprise at least eight or more fragrance chemicals, more likely to contain twelve or more and often twenty or more fragrance chemicals. The present invention also contemplates the use of complex fragrance formulations containing fifty or more fragrance chemicals, seventy five or more or even a hundred or more fragrance chemicals in a fragrance formulation.

Preferred fragrance materials will have both high ClogP and high vapor pressure. Among those having these properties are: Para cymene, Caphene, Mandarinal Firm, Vivaldie, Terpinene, Verdox, Fenchyl acetate, Cyclohexyl isovalerate, Manzanate, Myrcene, Herbavert, Isobutyl isobutyrate, Tetrahydrocitral, Ocimene and Caryophyllene.

According to one embodiment of the invention, the microcapsule particle composition is well suited for personal care and cleaning products. The present invention is also suitable for wash-off products, which are understood to be those products that are applied for a given period of time and then are removed. Products suitable for this invention are common in areas such as laundry products, and include detergents, fabric conditioners, and the like; as well as personal care products which include shampoos, hair rinses, body washes, soaps, hand sanitizers, anti-perspirants, deodorants and the like.

According to another embodiment of the invention the microcapsule composition is well suited for perfumes, eau de toilette and colognes. The appropriate carrier materials for the microcapsules in perfumes, eau de toilette and colognes include but are not limited to an aqueous or hydroalcoholic bases which includes alcohols such as ethanol, methanol, and the like; dipropylene glycol, dipropylene glycol ethers, diethyl phthalate and isopropyl myristate. The level of water in these systems is intentionally kept to a minimum, preferably below 5 weight percent of the fragrance composition, more preferably below 1 weight percent and most preferably less than 0.1 weight percent. Persons with skill in the art will be able to formulate fragrance compositions within the scope of the present invention that contain no intentionally added water.

Example of a suitable polymeric stabilizing agents useful in the present invention include carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum (including cationic guar gums such as Jaguar®), gum karaya, gum tragacanth, gum arabic, gum acacia, gum agar, xanthan gum and mixtures thereof. Preferred carbohydrate gums are the cellulose gums and xanthan gum.

In one embodiment, an anti-perspirant roll-on personal care product is provided which contains an effective amount of the microcapsule particle composition of the present invention.

As described herein, the present invention is well suited for use in a variety of well-known consumer products such as laundry detergent and fabric softeners, liquid dish detergents, automatic dish detergents, as well as hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos.

6,162,423, 5,968,286, 5,935561, 5,932,203, 5,837,661, 5,776,443, 5,756,436, 5,661,118, 5,618,523, 5,275,755, 5,085,857, 4,673,568, 4,387,090 and 4,705,681.

Sol-gel precursors, i.e. starting compounds capable of forming gels, suitable for the purposes of the invention are known per se to the expert. Sol-gel precursors usable in accordance with the invention are, for example, compounds, which are capable of forming gels, such as silicon, boron, aluminum, titanium, zinc, zirconium and vanadium. According to one embodiment, preferred sol-gel precursors are silicon, boron and aluminum compounds, more particularly organosilicon, organoboron and organoaluminum compounds. The precursors can also include metal alkoxides and b-diketonates Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

$(R_1O)(R_2O)M(X)(X')$, wherein X is equal to hydrogen or —OR$_3$; X' is equal to hydrogen or —OR$_4$; and R$_1$, R$_2$, R$_3$ and R$_4$ independently represent an organic group, more particularly a linear or branched alkyl group, preferably a C$_{1-12}$ alkyl. M can be Si, Ti, or Zr.

One example of a preferred sol/gel precursors suitable for the purposes of the invention are alkoxysilanes corresponding to the following general formula:

$(R_1O)(R_2O)Si(X)(X')$, wherein X is equal to hydrogen or —OR$_3$; X' is equal to hydrogen or —OR$_4$; and R$_1$, R$_2$, R$_3$ and R$_4$ independently represent an organic group, more particularly a linear or branched alkyl group, preferably a C$_{1-12}$ alkyl.

According to one embodiment, particularly preferred compounds are the silicic acid esters tetramethyl orthosilicate (TMOS) and tetraethyl orthosilicate (TEOS). A preferred compound includes Dynasylan® (commercially available from Degussa Corporation, Parsippany N.J., USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitated the utilization of this solubility property to load the dissolved molecules or substances in the monomeric precursor solvent or in the hydrolysis-condensation polymer of the monomer solvent. Nonetheless, the present invention may also be used to coat or load molecules or active ingredients which can be suspended in the precursors.

The particle size of the microcapsules may be in the range of 0.01-1000 microns in diameter, preferably 0.1-100 microns in diameter and more preferably 1-10 microns in diameter.

The wall thickness of the capsules can be controlled by varying the amount of monomer added. The ratio of monomer, such as TEOS, to that of oil phase, such as fragrance, may vary from about 2 to about 80 weight percent, preferably from about 5 to about 60 weight percent, more preferably from about 10 to about 50 weight percent, most preferably from about 15 to about 40 weight percent.

The water in the microcapsule particle composition may also be removed to provide a final product in powder form.

According to one embodiment of the present invention, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from about 1% to about 50%, more preferably from about 5% to about 20%.

Optionally, a free flow agent (anticaking agent) of silicas which may be hydrophobic (i.e. silanol surface treated with halogen silanes, alkoxysilanes, silazanes, siloxanes, etc. such as Sipernat D17, Aerosil R972 and R974 (available from Degussa), etc.) and/or hydrophilic such as Aerosil 200, Sipernat 22S, Sipernat 50S, (available from Degussa), Syloid 244 (available from Grace Davison), may be present from about 0.01% to about 10%, more preferable from 0.5% to about 5%.

Further suitable humectants and viscosity control/suspending agents are disclosed in U.S. Pat. Nos. 4,428,869, 4,464,271, 4,446,032, and 6,930,078 may also be incorporated. Details of hydrophobic silicas as a functional delivery vehicle of active materials other than a free flow/anticaking agent are disclosed in U.S. Pat. Nos. 5,500,223 and 6,608,017.

As described herein, the spray-dried microcapsule particle composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The spray drying inlet temperature is in the range of about 150° C. and about 240° C., preferably between about 170° C. and about 230° C., more preferably between about 190° C. and 220° C.

The present invention imparts a consumer benefit specifically relating to the different phase fragrance and/or benefit agent release: long-lasting benefit and/or fragrance perception via control release from capsules and relative immediate benefit and/or fragrance perception via release from water-soluble matrix dissolution. Also the change of sensory perception can be achieved due to the fragrance encapsulated in capsules could be different from that encapsulated in spray dry matrix. Finally, the high fragrance and/or benefit agent shelf life stability is made possible when spray-dried particles are placed in anhydrous bases with a minimal leaching.

All U.S. patents and patent applications cited herein are incorporated by reference as if set forth herein in their entirety.

The following examples are provided as specific embodiments of the present invention. These and additional modi-

EXAMPLE 1

Method A

Preparation of Silica Capsule by Direct Emulsification

Twelve grams tetraethyl orthsilicate (TEOS) was mixed with 140 g of fragrance oil (to form an oil phase and the mixture was cooled down in an ice-bath. The fragrance is suitable for personal care applications. In a separate vessel, 150 g of 0.5% aqueous surfactant (CTAC: cetyl trimethyl ammonium chloride obtained as 25% solution from Aldrich Chemical Company, Milwaukee, Wis., USA) solution was prepared by dissolving the needed amount of surfactant in distilled water and was also cooled down on an ice-bath. The oil phase was then poured into the aqueous phase and the mixture was homogenized using a high shear mixer (Ultra Turrax T 25 Basic, IKA, Werke). Four drops of defoamer was added to suppress the foam generated. The pH of the system is maintained around 3.9. The system was the left at room temperature and cured for an extended period of time. The capsule formed was well dispersed and generally has a particle size ranging from submicron to one hundred micron depending on the emulsifier and shear rate used.

Capsule can also be prepared without cooling the various mixtures. The amount of wall material can be easily adjusted by adjusting the amount of TEOS.

EXAMPLE 2

Method B

Preparation of Silica Capsule by Direct Emulsification of Oil, then Adding the TEOS: The 1-Step Post-Addition Process Step One. Preparation of Fragrance Emulsion.

140 g fragrance oil was placed in round bottom vessel and was cooled down in an ice-bath. In a separate vessel, 0.5% of aqueous surfactant solution (150 g) was prepared by dissolving the needed amount of solid surfactant in distilled water and was also cooled down on an ice-bath. The oil phase was then poured into the aqueous phase and the mixture was homogenized with a high shear mixer (Ultra Turrax T 25 Basic, IKA, Werke). Four drops of defoamer was added to suppress the foaming generated.

Step Two. Addition of TEOS to the Fragrance Emulsion.

Twenty four gram of wall forming TEOS was weighted out in a clean and dry vessel and was transferred into a dropping funnel. It was then added drop wise into the fragrance emulsion prepared in Step one under constant mixing. The mixing speed was reduced once the addition of TEOS was complete. The system was then left at room and cured for an extended period of time. The pH of the system is maintained around 3.9. The capsule formed was well dispersed and generally has a particle size ranging from submicron to one hundred micron depending on the emulsifier and shear rates used.

EXAMPLE 3

Method C

Preparation of Silica Capsule by Preparing Concentrated Fragrance Emulsification, Diluting the Fragrance Emulsion to Desired Concentration, and Adding the TEOS: The 2-Step Post-Addition Process Step One. Preparation of Concentrated Fragrance Emulsion.

This was achieved the same as step one on Example 4 using 140 g of the same fragrance.

Step Two: Preparation of Diluted Fragrance Emulsion.

This was achieved the by blending the emulsion prepared in step one of example 3 with the desired amount of water to generate the desired concentration.

Step Three. The Formation of Silica Capsules by Adding TEOS to the Diluted Fragrance Emulsion.

The amount of TEOS added in this step is normally determined by the wall polymer level needed and the amount of wall forming TEOS can be varied from 1% to 30% of the finished formulation.

Typically, the desired amount TEOS (24 g in this example) was weighted out and placed in a clean and dry dropping funnel. The TEOS was then added drop wise into the fragrance emulsion prepared in step two under constant mixing. The mixing speed was reduced once the addition of TEOS was complete. The system was the left at room and cured for an extended period of time. The pH of the system is maintained around 3.9. The capsule formed was well dispersed and generally has a particle size ranging from submicron to one hundred micron depending on the emulsifier and shear rates used.

EXAMPLE 4

Method D

Preparation of Silica Capsule by Adding TEOS Emulsion to Fragrance Emulsion Step One. Preparation of Fragrance Emulsion.

Four hundred grams of fragrance (Rapid leach, IPC, 31744979, IFF) emulsion containing 40% fragrance oil was prepared by emulsifying 160 g fragrance oil into 240 of surfactant (CTAC) solution. This fragrance emulsion can be further diluted to the desired fragrance concentration.

Step Two: Preparation of TEOS Emulsion.

Twenty four grams of TEOS was emulsified into a cooled aqueous surfactant solution (50 g) under shearing to give the TEOS emulsion. The surfactant used is a nonionic surfactant Witconol NP-90 (Akzo Nobel Surface Chemistry, Chicago, Ill., USA).

Step Three. Silica Capsule Formation by Adding TEOS Emulsion to Fragrance Emulsion.

The TEOS emulsion prepared in step two was added into the fragrance emulsion prepared in step one under constant mixing. The mixing speed was reduced once the addition of TEOS emulsion was complete. The system was the left at room temperature and cured for an extended period of time. The capsules formed were well dispersed and generally have a particle size ranging from submicron to one hundred micron depending on the emulsifier and shear rates used.

EXAMPLE 5

Method E

Preparation of Silica Capsule Using Sol-Gel Polymer by Pre-Hydrolysis of TEOS and Emulsification of Fragrance Oil Step One. Preparation of Sol-Gel Polymer by Hydrolysis of TEOS.

Fifty grams of TEOS was dissolved in 17.43 g of DI $H_2O$ and 44.35 g of Ethanol. The pH of the mixture was then adjusted to a pH of 2 with a 10% solution of HCl. The mixture was allowed to stir for 15 minutes after this time. The mixture was blended with fragrance once the phase separation disappeared.

Step Two: Preparation of Silica Capsule.

Two hundred seventy grams of fragrance oil suitable for personal care application was blended with 72 g of the sol-gel precursors and the mixture was directly emulsified into a cooled aqueous surfactant solution under shearing to give the fragrance emulsion. The system was then left at room and cured for an extended period of time. The capsules formed were well dispersed and generally had a particle size ranging from submicron to one hundred micron depending on the emulsifier and shear rates used.

EXAMPLE 6

Modification of Silica Capsules Using Second Sphere Complexation Using Polyethyleneimine (PEI) Polymer Preparation of Neutralized PEI Solution:

A 50% PEI (MW~750 kD, Aldrich Chemical Company, Milwaukee, Wis., USA) solution was pH adjusted to ~4 using concentrated HCl. The effective concentration of PEI was at 22% after the addition of HCl was complete.

Addition of PEI to Silica Capsule Slurry:

One hundred gram of the silica capsule slurry (from Example 1) was continuously stirred while 20 g of PEI solution (~22%, pH~4) was slowly added. The mixture was stirred at room temperature overnight.

EXAMPLE 7

Second Sphere Modification with a Nonionic Amine Oxide Surfactant

Preparation of Neutralized CDO Special Solution:

Ammonyx® CDO Special, or cocoamidopropylamine oxide, was obtained from the Stephan Company (Chicago, Ill., USA) and contains 32.5% active ingredient. The concentrated solution was pH adjusted to ~4 using 10N HCl. The final concentration of amine oxide was 29% after it was neutralization.

Addition of CDO Special to Silica Capsule Slurry:

One hundred of silica capsule slurry (from Example 1) was continuously stirred while 5.8 g of Ammonyx® CDO Special solution (~29% active, pH~4) was slowly added. The mixture was stirred at room temperature overnight and used for further application studies.

EXAMPLE 8

Second Sphere Modification of Silica Capsules with an Anionic Surfactant

Ammonium Lauryl Ether Sulfate (STEOL CA-300)

Preparation of Neutralized STEOL CA-300 Solution:

Ammonium lauryl ether sulfate solution (STEOL® CA-330) was obtained from Stephan (Chicago, Ill.) which has 28% active. The pH of the solution was adjusted to ~pH 4 using 1N HCl. With the addition of HCl, the concentration of the active compounds decreased to ~27%.

Addition of STEOL to Silica Capsule Slurry:

100 g of silica capsule slurry (from Example 1) of 100 g was continuously stirred while 6.3 g of STEOL® CA-330 solution (~27% active, pH~4) was added to it and the mixture was stirred overnight and used for further experiments.

EXAMPLE 9

Second Sphere Modification of Silica Capsules with Inorganic Nanoparticle

Zinc Oxide

To 100 g Silica capsule slurry (from Example 1) was added 0.1 g Z-COTE HP1 (BASF), the particle size of ZnO was less than 200 nm. The mixture was overhead stirred at room temperature overnight.

EXAMPLE 10

Evaluation of Capsule Stability by Microscopy

The stability of the capsules was evaluated by diluting the slurry with water. The diluted sample was placed on a microscopic slide and monitored overnight. The results are given in FIGS. 10A to 10F. The microscopic picture in FIG. 10A depicts well formed silica capsules as fresh sample in water. Some breakage of the capsules was seen after the capsules were dried overnight on a microscopy slide as illustrated in FIG. 10B. Damage to capsules was also observed using SEM (FIG. 10C) and when a vacuum was applied and the capsules was dried to some extent.

An optical picture of sample prepared using example 6 was presented in FIG. 10 D and it clearly shows the capsules retained their structural integrity after drying overnight in a microscopy slide. The picture taken using SEM further confirmed that the robustness of the capsules was dramatically improved as compared with FIG. 10C.

The procedure in example 7 was also used to prepare stabilized capsule slurry and the optical (FIG. 10F) and SEM (10G) showed that capsules retained its structural integrity after being dried overnight.

We also found the second sphere modification of silica capsules using ZnO can increase the stability of the capsules and the result is demonstrated in FIG. 10H.

EXAMPLE 11

Encapsulation Performance of Mechanically Stable Silica Capsules

The sample prepared in example 6 was evaluated for its performance by head space analysis. The fragrance capsule slurry was diluted with distilled water to yield a mixture containing 0.4% capsule slurry. One gram each of the diluted capsule slurry was directed applied to each side of a 4×6 fabric swatch. Three samples were evaluated. They are neat fragrance (neat), capsule from example 3 (no modification) without the second sphere modification, and a sample from example 6 were prepared (modified capsule). The swatches were air-dried over night and the headspace of the fabrics was analyzed before and after stirring with steel ball bearings to rupture intact capsules. The results are given in table 1 below.

TABLE 1

Encapsulation performance of the modified silica capsules

| Sample | Head space Unstirred | Head space Stirred | Ratio of Stirred/Unstirred |
|---|---|---|---|
| Neat fragrance | 4400 | 6600 | 1.5 |
| Unmodified capsules | 3600 | 8050 | 2.23 |
| Modified capsules | 2350 | 16000 | 6.80 |

It can be clearly seen that there is a dramatic increase in headspace after the capsules were disrupted by milling in the modified silica capsules. The ratio of stirred/unstirred sample increased by 200 percent in the modified capsules. This demonstrated that increase perfumery perception can be achieved once the capsules are deposited on fabric.

EXAMPLE 12

Sensory Performance of Mechanically Stable Silica Capsules

The sample prepared in example 6 was evaluated for its performance by an trained internal panel The fragrance capsule slurry was diluted with distilled water to yield a mixture containing 0.4% capsule slurry. One gram each of the diluted capsule slurry was directed applied to each side of a 4×6 fabric swatch. The swatches were air-dried over night and the evaluated by the internal panel of 12 judges. The fragrance intensity is rated from a scale ranging from 0 to 30. A numerical value of 5 would suggest the fabric only produce very week intensity while a value of 30 indicates the subject generate a strong smell. Three samples were evaluated. They are neat fragrance (neat), capsule from example 3 (no modification) without the second sphere modification, and a sample from example 6 were prepared (modified capsule). The results are in Table 3.

TABLE 3

Contrasting the Sensory performance of capsules with that of neat fragrance and unmodified capsules

| Samples | Pre-rubbing intensity | Post-rubbing intensity | $I_{post}/I_{pre}$ |
|---|---|---|---|
| Neat | 6.0 | 6.5 | 1.1 |
| Unmodified capsules | 6.0 | 6.0 | 1.0 |
| Modified capsules | 4.0 | 16.0 | 4.0 |

It is quite apparent the modified silica fragrance capsules produced much greater fragrance intensity at post-rubbing stages stage. The ratio of intensity ($I_{post}/I_{pre}$) in the coated capsule is four times that of the neat and uncoated capsules. This demonstrates that the modified fragrance capsules prepared with the current invention are able to retain the fragrance effectively and are capable of delivering the full consumer benefits of the fragrance products.

EXAMPLE 13

Benefit of the Microcapsule Particle Composition in a Personal Care Application

This example illustrates the application benefit of the capsules prepared by the process in Example 9 in antiperspirent (AP) roll-on base. Fragrance capsule slurry was prepared using the process described in Example 9. The capsule slurry was dispersed in a AP-roll base at 0.5% neat fragrance equivalent. The base typically contained 1 to 3% anionic surfactant, 10 to 20%, aluminum chlorohydrate, less than 1% silica, 1 to 2% *Helianthus Annuus* and water.

The prepared product containing the capsule (100 ul) in AP roll-on based was applied to the forearm of six panelists and the fragrance intensity was evaluated immediately after application and five hours after application with rubbing by 20 trained intensity judges and data was analyzed statistically. The fragrance intensity is rated from a scale ranging from 0 to 30. A numerical value of 5 would suggest the substrate only produce very week intensity while a value of 30 indicates the subject generate a strong smell.

It was found that, after rubbing the product containing capsule generated greater fragrance intensity before rubbing after five hours and significantly greater intensity after rubbing than a product containing neat fragrance only. The post rubbing intensity of the capsule product is 150% that of the neat fragrance product. When repeated measures analysis of variance is used to analyze the data. There is significant difference between the capsule and neat when significance level is set at p<0.01. Results are provided below in Table 4. This clearly demonstrate that the modified capsule in the current invention can deliver superior consumer befits when compared to the use of neat fragrance.

TABLE 4

Fragrance benefits of the capsules prepared by current invention

| Sample | Fragrance intensity immediately after application | Fragrance intensity 5 hours after application without rubbing, $I_{pre}$ | Fragrance intensity 5 hours after application with rubbing, $I_{post}$ | Ratio of $I_p$, neat/$I_{capsule}$ |
|---|---|---|---|---|
| Neat fragrance | 18.0 | 8.7 | 7.0 | 1 |
| Capsules prepared by the current invention from Example 9 | 16.0 | 9.2 | 10.5 | 1.5 |

Storage test conducted simultaneously indicated that there is only 10% fragrance leach out of the capsule after 5 weeks at 37° C. These results clearly established the excellent consumer benefits and long term stability of the capsules prepared by our invention.

What is claimed:

1. A process for preparing a silica microcapsule particle composition comprising the steps of:
   (a) preparing a mixture of a silica sol-gel precursor and an active material;

(b) preparing a surfactant solution by dissolving a surfactant in water;
(c) adding the silica sol-gel precursor and active material mixture obtained in step (a) to the surfactant solution obtained in step (b);
(d) homogenizing the mixture of silica sol-gel precursor, active material and surfactant solution obtained in step (c);
(e) curing the homogenized mixture to form silica microcapsule particles; and
(f) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

2. The process of claim 1, further comprising adding a defoamer to the homogenized mixture obtained in step (d).

3. The process of claim 1, wherein the active material is a fragrance.

4. The process of claim 1, wherein the silica sol-gel precursor is selected from a metal or semi-metal alkoxide monomer, or metal ester monomer, semi-metal ester monomer or alkoxysilanes monomer corresponding to the general formula:

$(R_1O)(R_2O)M(X)(X')$, wherein M is equal to Si; X is equal to —$OR_3$; X' is equal to —$OR_4$; and $R_1$, $R_2$, $R_3$ and $R_4$ independently represent a linear or branched $C_{1-12}$ alkyl group.

5. The process of claim 1, wherein the silica sol-gel precursor is selected from the group consisting of tetramethyl orthosilicate, tetraethyl orthosilicate and mixtures thereof.

6. The process of claim 1, further comprising the step of removing water to obtain a final product in a powder form.

7. A silica microcapsule particle composition obtained by a process comprising the steps of:
(a) preparing a mixture of a silica sol-gel precursor and an active material;
(b) preparing a surfactant solution by dissolving a surfactant in water;
(c) adding the silica sol-gel precursor and active material mixture obtained in step (a) to the surfactant solution obtained in step (b);
(d) homogenizing the mixture of silica sol-gel precursor, active material and surfactant solution obtained in step (c);
(e) curing the homogenized mixture to form silica microcapsule particles; and
(f) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

8. A consumer product comprising the silica microcapsule particle composition of claim 7, wherein the consumer product is selected from the group consisting of shampoos, hair rinses, body washes, soaps, hand sanitizers, liquid dish detergents, automatic dish detergents, anti-perspirants and deodorants.

9. The consumer product of claim 8, wherein the product is an anti-perspirant.

10. A process for preparing a silica microcapsule particle composition comprising the steps of:
(a) adding a fragrance oil to an aqueous surfactant solution to form a mixture;
(b) homogenizing the mixture obtained in step (a) to form a fragrance emulsion;
(c) adding a silica sol-gel precursor to the fragrance emulsion;
(d) curing the mixture obtained in step (c) to form silica microcapsule particles,
(e) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

11. The process of claim 10, wherein the silica sol-gel precursor is selected from a metal or semi-metal alkoxide monomer, or metal ester monomer, semi-metal ester monomer or alkoxysilanes monomer corresponding to the general formula:

$(R_1O)(R_2O)M(X)(X')$, wherein M is equal to Si; X is equal to —$OR_3$; X is equal to —$OR_4$; and $R_1$, $R_2$, $R_3$ and $R_4$ independently represent a linear or branched $C_{1-12}$ alkyl group.

12. The process of claim 10, wherein the silica sol-gel precursor is selected from the group consisting of tetramethyl orthosilicate, tetraethyl orthosilicate and mixtures thereof.

13. The process of claim 10 further comprising the step of removing the water to obtain a final product in a powder form.

14. A silica microcapsule particle composition obtained by a process comprising the steps of:
(a) adding a fragrance oil to an aqueous surfactant solution to form a mixture;
(b) homogenizing the mixture obtained in step (a) to form a fragrance emulsion;
(c) adding a silica sol-gel precursor to the fragrance emulsion;
(d) curing the mixture obtained in step (c) to form silica microcapsule particles,
(e) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

15. A consumer product comprising the silica microcapsule particle composition of claim 14, wherein the consumer product is selected from the group consisting of shampoos, hair rinses, body washes, soaps, hand sanitizers, liquid dish detergents, automatic dish detergents, anti-perspirants and deodorants.

16. The consumer product of claim 15, wherein the product is an anti-perspirant.

17. A process for preparing a silica microcapsule particle composition comprising the steps of:
(a) adding a fragrance oil to an aqueous surfactant to form a mixture;

(b) homogenizing the mixture obtained in step (a) to form a fragrance emulsion;
(c) adding water to the fragrance emulsion obtained in step (b) to achieve a diluted fragrance emulsion;
(d) adding a silica sol-gel precursor to the diluted fragrance emulsion obtained in step (c);
(e) curing the mixture obtained in step (d) until silica microcapsule particles are formed; and
(f) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

18. The process of claim 17, wherein the silica sol-gel precursor is selected from a metal or semi-metal alkoxide monomer, or metal ester monomer, semi-metal ester monomer or alkoxysilanes monomer corresponding to the general formula:

$$(R_1O)(R_2O)M(X)(X')$$

wherein M is equal to Si; X is equal to —$OR_3$; X is equal to —$OR_4$; and $R_1$, $R_2$, $R_3$ and $R_4$ independently represent a linear or branched $C_{1-12}$ alkyl group.

19. The process of claim 17, wherein the silica sol-gel precursor is selected from the group consisting of tetramethyl orthosilicate, tetraethyl orthosilicate and mixtures thereof.

20. The process of claim 17, further comprising the step of removing water to obtain a final product in a powder form.

21. A silica microcapsule particle composition obtained by a process comprising the steps of:
(a) adding a fragrance oil to an aqueous surfactant to form a mixture;
(b) homogenizing the mixture obtained in step (a) to form a fragrance emulsion;
(c) adding water to the fragrance emulsion obtained in step (b) to achieve a diluted fragrance emulsion;
(d) adding a silica sol-gel precursor to the diluted fragrance emulsion obtained in step (c);
(e) curing the mixture obtained in step (d) until silica microcapsule particles are formed; and
(f) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

22. A consumer product comprising the silica microcapsule particle composition of claim 21, wherein the consumer product is selected from the group consisting of shampoos, hair rinses, body washes, soaps, hand sanitizers, liquid dish detergents, automatic dish detergents, anti-perspirants and deodorants.

23. The consumer product of claim 22, wherein the product is an anti-perspirant.

24. A process for preparing a silica microcapsule particle composition comprising the steps of:
(a) preparing a fragrance emulsion by emulsifying a fragrance oil into a surfactant solution;
(b) preparing a silica sol-gel precursor emulsion by emulsifying a silica sol-gel precursor and an aqueous surfactant solution;
(c) adding the silica sol-gel precursor emulsion formed in step (b) to the fragrance emulsion obtained in step (a);
(d) curing the mixture obtained in step (c) until silica microcapsule particles are formed; and
(e) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

25. The process of claim 24, wherein the silica sol-gel precursor is selected from a metal or semi-metal alkoxide monomer, or metal ester monomer, semi-metal ester monomer or alkoxysilanes monomer corresponding to the general formula:

$$(R_1O)(R_2O)M(X)(X')$$

wherein M is equal to Si; X is equal to —$OR_3$; X is equal to —$OR_4$; and $R_1$, $R_2$, $R_3$ and $R_4$ independently represent a linear or branched $C_{1-12}$ alkyl group.

26. The process of claim 24, wherein the silica sol-gel precursor is selected from the group consisting of tetramethyl orthosilicate, tetraethyl orthosilicate and mixtures thereof.

27. The process of claim 24, further comprising the step of removing water to obtain a final product in a powder form.

28. A silica microcapsule particle composition obtained by a process comprising the steps of:
(a) preparing a fragrance emulsion by emulsifying a fragrance oil into a surfactant solution;
(b) preparing a silica sol-gel precursor emulsion by emulsifying a silica sol-gel precursor and an aqueous surfactant solution;
(c) adding the silica sol-gel precursor emulsion formed in step (b) to the fragrance emulsion obtained in step (a);
(d) curing the mixture obtained in step (c) until silica microcapsule particles are formed; and
(e) modifying the silica microcapsule particles with a sphere complexation to form a silica microcapsule particle composition containing coated silica microcapsule particles, wherein the sphere complexation is a polyethyleneimine polymer, a lauryl ether sulfate, an inorganic zinc oxide, or a mixture thereof, and the sphere complexation is present at a level of 0.1% or greater by weight of the composition.

29. A consumer product comprising the microcapsule particle composition of claim 28, wherein the consumer product is selected from the group consisting of shampoos, hair rinses, body washes, soaps, hand sanitizers, liquid dish detergents, automatic dish detergents, anti-perspirants and deodorants.

30. The consumer product of claim 29, wherein the product is an anti-perspirant.

* * * * *